(12) United States Patent
Tang et al.

(10) Patent No.: US 11,380,454 B2
(45) Date of Patent: Jul. 5, 2022

(54) JAW POSITION DETECTION APPARATUS AND MEDICAL ACCELERATOR TREATMENT HEAD

(71) Applicant: OUR UNITED CORPORATION, Shaanxi (CN)

(72) Inventors: Ziming Tang, Shaanxi (CN); Zhao Guo, Shaanxi (CN); Yueming Yang, Shaanxi (CN)

(73) Assignee: OUR UNITED CORPORATION

( * ) Notice: Subject to any disclaimer, the term of this patent is extended or adjusted under 35 U.S.C. 154(b) by 112 days.

(21) Appl. No.: 16/979,907

(22) PCT Filed: Jun. 13, 2019

(86) PCT No.: PCT/CN2019/091163
§ 371 (c)(1),
(2) Date: Sep. 11, 2020

(87) PCT Pub. No.: WO2020/103437
PCT Pub. Date: May 28, 2020

(65) Prior Publication Data
US 2021/0012918 A1    Jan. 14, 2021

(30) Foreign Application Priority Data
Nov. 20, 2018 (CN) .......................... 201811386598.7

(51) Int. Cl.
*G21K 1/02* (2006.01)
*G01D 5/02* (2006.01)
*A61N 5/10* (2006.01)

(52) U.S. Cl.
CPC ........... *G21K 1/025* (2013.01); *A61N 5/1043* (2013.01); *A61N 5/1065* (2013.01); *G01D 5/02* (2013.01); *A61N 5/1048* (2013.01); *A61N 5/1078* (2013.01)

(58) Field of Classification Search
CPC ...... A61N 5/10; A61N 5/1042; A61N 5/1043; A61N 5/1064; A61N 5/1065; A61B 6/06;
(Continued)

(56) References Cited

U.S. PATENT DOCUMENTS 3,115,580 A * 12/1963 Brewer .................... G21K 1/04
                                              976/DIG. 428
6,730,924 B1 * 5/2004 Pastyr ...................... G21K 1/04
                                              378/150
(Continued)

FOREIGN PATENT DOCUMENTS

CN        106134311 B     10/2013
CN        204255321 U      4/2015
(Continued)

OTHER PUBLICATIONS

International Search Report dated Sep. 11, 2019 in corresponding PCT International Application No. PCT/CN2019/091163.
(Continued)

*Primary Examiner* — Anastasia Midkiff
(74) *Attorney, Agent, or Firm* — Ostrolenk Faber LLP

(57) ABSTRACT

A jaw position detection apparatus is configured to detect position information of at least one jaw moving in an arc, and includes a connecting component, a conversion mechanism, and a displacement sensor. The connecting component is fixed on a jaw. The conversion mechanism is connected to the connecting component, and the conversion mechanism is configured to convert an arc motion of the connecting component into a linear motion when the connecting component moves in an arc with the jaw. The displacement sensor is connected to the conversion mechanism, and configured to detect displacement information of the linear motion of the conversion mechanism.

20 Claims, 3 Drawing Sheets

(58) Field of Classification Search
CPC ....... A61B 6/40; A61B 6/405; A61B 2560/02; A61B 2560/04; A61B 2560/06; G02B 5/00; G02B 5/005; G02B 7/20; G02B 7/24; G02B 26/08; G02B 26/10; G02B 27/09; G02B 27/0938; G02B 27/0988; G02B 27/30; G01D 5/02; G01D 5/04; G01D 11/30; G01D 2205/10; G01D 2205/14; G01D 2205/20; G01D 2205/22; G01D 2205/26; G01D 2205/28; G01N 2223/30; G01N 2223/316; G01N 2223/33; G01N 2223/3301; G21K 1/02; G21K 1/025; G21K 1/04; G21K 1/043; H01J 35/14; H01J 2237/04; H01J 2237/045; H01J 2237/0455; H01J 2237/0456; H01J 2237/0458; H01J 2237/083; H01J 2237/0835; H01J 2237/15; H01J 2237/1502; H01J 2237/1503; H01J 2237/2482

See application file for complete search history.

(56) References Cited

U.S. PATENT DOCUMENTS

2006/0050843 A1\* 3/2006 Strommer .............. A61B 6/502
378/37
2011/0049395 A1\* 3/2011 Hashimoto .......... A61N 5/1045
250/505.1

FOREIGN PATENT DOCUMENTS

| CN | 105391368 A | 3/2016 |
|---|---|---|
| CN | 205352295 U | 6/2016 |
| JP | 2011-036477 A | 2/2011 |
| JP | 4996450 B2 | 8/2012 |

OTHER PUBLICATIONS

Written Opinion dated Sep. 11, 2019 in corresponding PCT International Application No. PCT/CN2019/091163.

\* cited by examiner

JAW POSITION DETECTION APPARATUS AND MEDICAL ACCELERATOR TREATMENT HEAD

CROSS-REFERENCE TO RELATED APPLICATIONS

This application is a national phase entry under 35 USC 371 of International Patent Application No. PCT/CN2019/091163 filed on Jun. 13, 2019, which claims priority to Chinese Patent Application No. 201811386598.7, filed with the Chinese Patent Office on Nov. 20, 2018, titled "JAW POSITION DETECTION APPARATUS AND MEDICAL ACCELERATOR TREATMENT HEAD", which are incorporated herein by reference in their entireties.

TECHNICAL FIELD

The present disclosure relates to the technical field of medical equipment, and in particular, to a jaw position detection apparatus and a medical accelerator treatment head.

BACKGROUND

A jaw of a medical accelerator treatment head is driven by a motor to control output doses of X-rays through opening and closing of the jaw. Therefore, in order to accurately control motion of the jaw of the medical accelerator treatment head, a specific position of the jaw of the medical accelerator treatment head needs to be detected in real time.

In order to reduce a radiation penumbra of the X-rays, it is required that an inner surface of the jaw is always tangent to the X-rays when the jaw moves at any angle, so that the jaw generally moves in an arc. In order to detect the position of the jaw moving in the arc, an encoder is generally used in the related art. A chip is integrated inside the encoder, which may convert angular displacements into electrical signals to obtain the position of the jaw.

SUMMARY

Some embodiments of the present disclosure provide a jaw position detection apparatus. The following technical solutions are adopted:

On one hand, some embodiments of the present disclosure provide a jaw position detection apparatus, configured to detect position information of at least one jaw moving in an arc. The jaw position detection apparatus includes a connecting component, a conversion mechanism, and a displacement sensor. The connecting component is fixed on a jaw. The conversion mechanism is connected to the connecting component. The conversion mechanism is configured to convert an arcuate motion of the connecting component into a linear motion when the connecting component moves in an arc with the jaw. The displacement sensor is connected to the conversion mechanism, and configured to detect displacement information of the linear motion of the conversion mechanism.

The jaw position detection apparatus in some embodiments of the present disclosure includes a connecting component, a conversion mechanism and a displacement sensor, and the connecting component is fixed on the jaw to move in an arc with the jaw. The conversion mechanism is connected to the connecting component, and the conversion mechanism converts an arc motion of the connecting component into a linear motion when the connecting component moves in an arc with the jaw, and the displacement sensor connected to the conversion mechanism may directly detect displacement information of the linear motion of the conversion mechanism. In this way, through the displacement information detected by the displacement sensor, the position information of the jaw may be obtained to realize the detection of the position of the jaw. Compared with the related art, the arcuate motion of the jaw is converted into the linear motion of the conversion mechanism, so that the detection may be achieved by using the displacement sensor. A basic principle of the displacement sensor is a sliding resistor, in which device(s) such as chip(s) that is not resistant to X-ray irradiation is not contained, and thus the displacement sensor can adapt to a large amount of irradiation and is not easily damaged. Moreover, the displacement sensor has a higher detection accuracy than the encoder.

On the other hand, some embodiments of the present disclosure further provide a medical accelerator treatment head. The medical accelerator treatment head includes at least one jaw moving in an arc, and further includes a jaw position detection apparatus. The jaw position detection apparatus includes a connecting component, a conversion mechanism, and a displacement sensor. The connecting component is fixed on a jaw. The conversion mechanism is connected to the connecting component. The conversion mechanism is configured to convert an arcuate motion of the connecting component into a linear motion when the connecting component moves in an arc with the jaw. The displacement sensor is connected to the conversion mechanism, and configured to detect displacement information of the linear motion of the conversion mechanism.

On the other hand, some embodiments of the present disclosure further provide a medical accelerator treatment head. The medical accelerator treatment head includes at least one jaw moving in an arc, and further includes a jaw position detection apparatus. The jaw position detection apparatus includes a connecting component, a conversion mechanism, and a displacement sensor. The connecting component is fixed on a jaw. The conversion mechanism is connected to the connecting component. The conversion mechanism is configured to convert an arcuate motion of the connecting component into a linear motion when the connecting component moves in an arc with the jaw. The displacement sensor is connected to the conversion mechanism, and configured to detect displacement information of the linear motion of the conversion mechanism. The medical accelerator treatment head further includes at least one motor, two arc gear rings and a plurality of rotary gears. Two rotary gears are disposed at two sides of each jaw corresponding to the two arc gear rings, and the two rotary gears are matched with the two arc gear rings; the two rotary gear are configured to move in an arc along the two arc gear rings under driving of a motor.

Since the jaw moves in an arc, after the medical accelerator treatment head provided by some embodiments of the present disclosure includes the above jaw position detection apparatus, the medical accelerator treatment head may effectively detect the position information of the jaw, is able to adapt to a large amount of irradiation, is not easily damaged and has a high detection accuracy.

BRIEF DESCRIPTION OF THE DRAWINGS

In order to more clearly illustrate the technical solutions of the embodiments of the present disclosure, the drawings used in the embodiments and the related art descriptions will be briefly described below. Obviously, the drawings in the following description are merely some embodiments of the present disclosure, and other drawings can be obtained by those skilled in the art according to these drawings without paying any creative effort.

DETAILED DESCRIPTION

The technical solutions in the embodiments of the present disclosure will be described clearly and completely with reference to the accompanying drawings in the embodiments of the present disclosure. Obviously, the described embodiments are merely some but not all of the embodiments of the present disclosure. All other embodiments obtained on the basis of the embodiments of the present disclosure by a person of ordinary skill in the art without paying any creative effort shall be included in the protection scope of the present disclosure.

The terms "first" and "second" are only used for describing purposes, and cannot be construed as indicating or implying relative importance or implicitly indicating the number of technical features indicated. Thus, features defined with "first" and "second" may explicitly or implicitly include one or a plurality of the features. In the description of the present disclosure, "a plurality of" means two or more unless otherwise specified.

In the description of the present disclosure, it will be noted that the terms "mounted" and "connected" should be understood broadly unless specifically stated or defined otherwise, for example, a fixed connection, a detachable connection, or an integral connection. The specific meanings of the above terms in the present disclosure can be understood by those ordinary skilled in the art according to specific situations.

In the related art, the detection accuracy of the encoder is not high, and dose of X-rays is relatively large when the medical accelerator treatment head is in operation, which causes great interference to the transmission of signals of the chip in the encoder, thereby further reducing the detection accuracy. In addition, since the chip is used in a large amount of irradiation for a long time, the chip is easily damaged.

Figure 1:
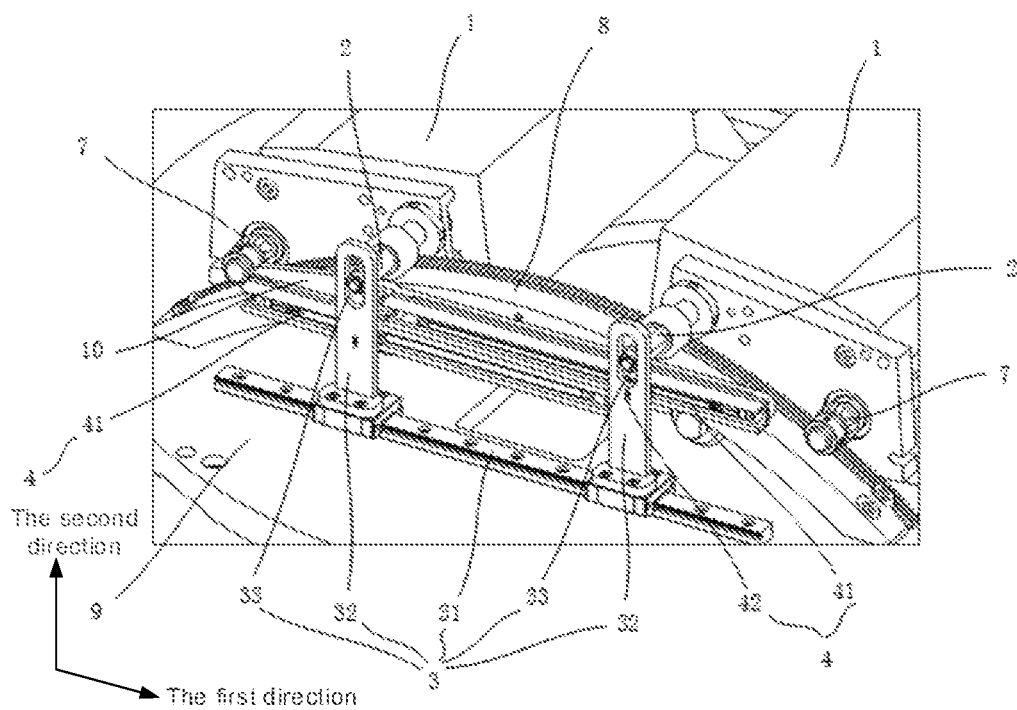
FIG. 1 is a schematic diagram showing a structure of a jaw position detection apparatus, according to some embodiments of the present disclosure.
Figure 2:
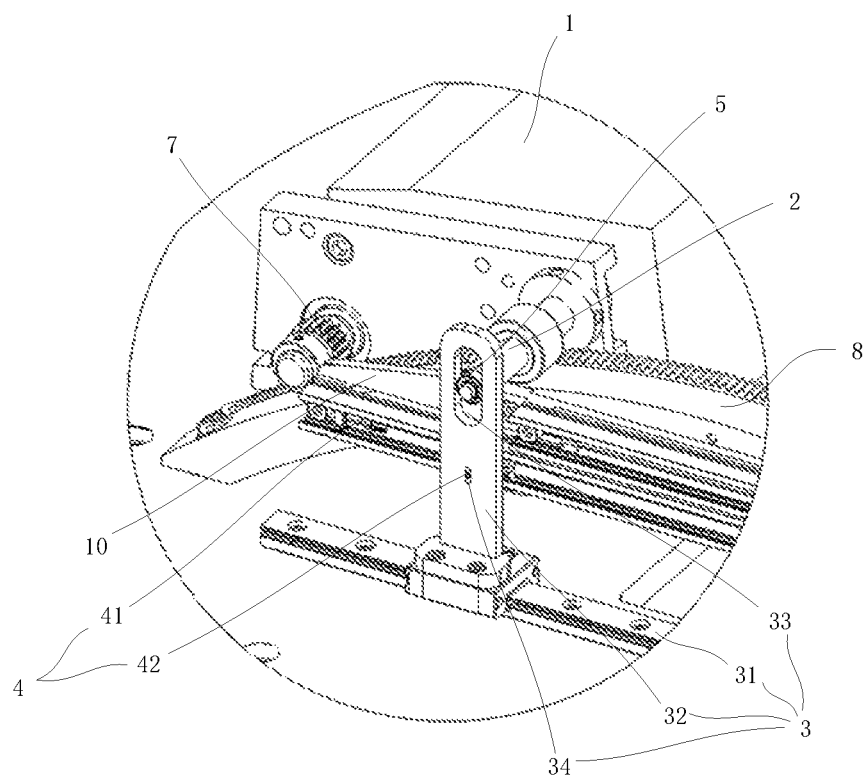
FIG. 2 is a schematic diagram showing a structure of a jaw position detection apparatus in Embodiment 1, according to some embodiments of the present disclosure.

Therefore, on one hand, a jaw position detection apparatus provided by some embodiments of the present disclosure, as shown in FIGS. 1 and 2, is configured to detect position information of jaws 1 moving in an arc. The jaw position detection apparatus in some embodiments of the present disclosure includes connecting components 2, a conversion mechanism 3, and displacement sensors 4. The connecting component 2 is fixed on the jaw 1. An input end of the conversion mechanism 3 is connected to the connecting component 2. When the connecting component 2 moves in the arc with the jaw 1, the conversion mechanism 3 converts an arcuate motion of the connecting component 2 into a linear motion. The displacement sensor 4 is connected to an output end of the conversion mechanism 3, and configured to detect displacement information of the linear motion of the output end of the conversion mechanism.

The jaw position detection apparatus in some embodiments of the present disclosure, as shown in FIGS. 1 and 2, includes connecting components 2, a conversion mechanism 3 and displacement sensors 4, and the connecting component 2 is fixed on the jaw 1 to move in an arc with the jaw. An input end of the conversion mechanism 3 is connected to the connecting component 2, and the conversion mechanism 3 converts an arcuate motion of the connecting component 2 into a linear motion when the connecting component 3 moves in an arc with the jaw 1, and the displacement sensor 4 connected to an output end of the conversion mechanism 3 may directly detect displacement information of the linear motion of the output end of the conversion mechanism 3. In this way, through the displacement information detected by the displacement sensor 4, the position information of the jaw 1 may be obtained to realize the detection of positions of the jaw 1. Compared with the related art, in some embodiments of the present disclosure, the arcuate motion of the jaw 1 is converted into the linear motion of the output end of the conversion mechanism 3, so that the detection may be achieved by using the displacement sensor 4. A basic principle of the displacement sensor 4 is a sliding resistor, in which device(s) such as chip(s) that is not resistant to X-ray irradiation is not contained, and thus the displacement sensor 4 can adapt to a large amount of irradiation and is not easily damaged. Moreover, the displacement sensor 4 has a higher detection accuracy than the encoder.

The conversion mechanism 3 may have a plurality of implementations, and two implementations are introduced as examples.

Embodiment 1

In the jaw position detection apparatus of the present embodiment, as shown in FIGS. 1 and 2, the conversion mechanism 3 includes a linear guide 31 extending in a first direction and sliding components 32 slidable along the linear guide 31. The sliding component 32 is provided with a first sliding groove 33 and a second sliding groove 34 along a second direction, an end portion of the connecting component 2 is matched with and extended into the first sliding groove 33, and the displacement sensor 4 is connected to the second sliding groove 34. The second direction is perpendicular to the first direction.

In this way, when the connecting component 2 moves in the arc with the jaw 1, the force pushing the sliding component 32 may be decomposed into a force in the first direction and a force in the second direction, which are perpendicular to each other. The force in the second direction causes an end portion of the connecting component 2 to slide in the second direction in the first sliding groove 33, and the force in the first direction causes the connecting component 2 to push an inner wall of the first sliding groove 33, which extends in the second direction, thereby causing the sliding component 32 to slide linearly in the first direction, and thus converting the arcuate motion of the connecting component 2 into a linear sliding. In addition, the displacement sensor 4 is connected to the second sliding groove 34, so that the displacement sensor 4 may detect displacement information of the linear sliding to obtain the position information of the jaw 1. The linear guide 31 may guide and limit the sliding of the sliding component 32.

It will be noted that, by providing the second sliding groove 34, a connection manner between the displacement sensor 4 and the output end of the conversion mechanism 3 is a form of matching with a sliding groove, which facilitates assembly. Moreover, the second sliding groove 34 may prevent relevant moving components of the displacement sensor 4 from being stuck.

In order to ensure that the connecting component 2 does not touch the inner wall of the first sliding groove 33 extending in the first direction when the connecting component 2 slides along the first sliding groove 33, and a normal motion of the connecting component 2 is not blocked, a distance of the first sliding groove 33 extending in the second direction is greater than or equal to a displacement of the connecting component 2 in the second direction when the connecting component 2 moves in the arc. In this way, the displacement of the connecting component 2 moving in the second direction is less than the distance of the first sliding groove extending in the second direction, so that the motion of the connecting component 2 is not blocked.

Figure 3:
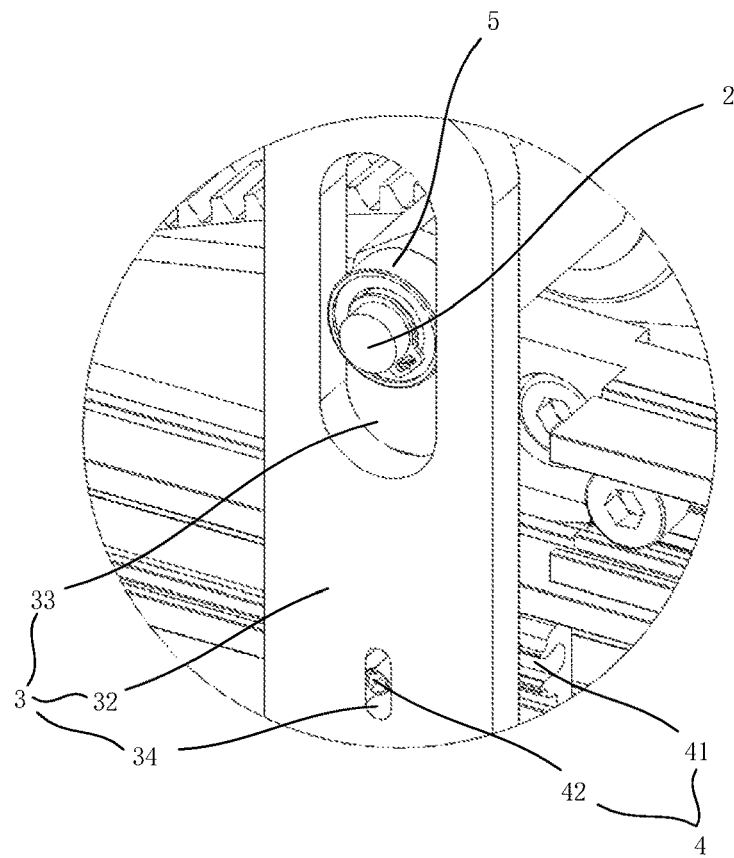
FIG. 3 is a schematic diagram showing a local structure of the jaw position detection apparatus in Embodiment 1, according to some embodiments of the present disclosure.

The motion of the connecting component 2 is the arcuate motion, and when the end portion of the connecting component 2 moves in the first sliding groove 33, the connecting component 2 will not only slide in the first sliding groove 33 in the second direction, but also rotate at a certain angle. Therefore, in order to reduce friction between the end portion of the connecting component 2 and the first sliding groove 33 to facilitate transmission of a mechanism force, as shown in FIG. 3, the end portion of the connecting component 2 is sleeved with a bearing 5, and an outer wall of the bearing 5 abuts against the inner wall of the first sliding groove 33, which extends in the second direction. The arrangement of the bearing 5 may well adapt to the sliding and rotation of the end portion of the connecting component 2 in the first sliding groove 33, so as to reduce friction, facilitate the transmission of force, and ensure the detection accuracy.

Here, the bearing 5 may be a rolling bearing, or may be any other bearing, which is not specifically limited in the embodiments of the present disclosure.

A structure of the displacement sensor 4 is shown in FIGS. 2 and 3. The displacement sensor 4 includes a variable resistance sliding rail 41 and an extension shaft 42. The variable resistance sliding rail 41 extends in the first direction, and a first end of the extension shaft 42 is slidable along the variable resistance sliding rail 41, and a second end of the extension shaft is fixedly connected to the second sliding groove 34 of the sliding component 32. In this way, when the sliding component 32 moves linearly, the extension shaft 42 is pulled to slide along the variable resistance sliding rail 41, so that a resistance value changes, and thus the displacement information of the linear sliding may be detected.

Further, the variable resistance sliding rail 41 of the displacement sensor 4 may be directly mounted on an arc gear ring 8, or may be mounted on a sensor mounting base 10 as shown in FIGS. 1 and 2, and the sensor mounting base 10 is mounted on the arc gear ring 8.

Here, the displacement sensor 4 may be a linear displacement sensor, or may be any other displacement sensor that may implement this function, which is not specifically limited in the present embodiment.

Embodiment 2

Figure 6:
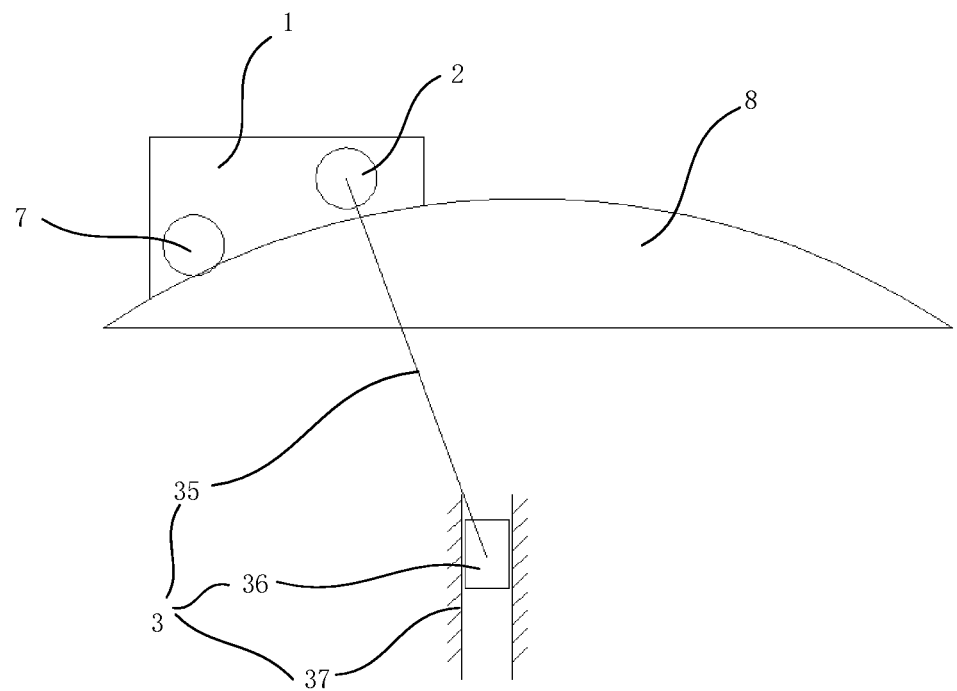
FIG. 6 is a schematic diagram showing a structure of a jaw position detection apparatus in Embodiment 2, according to some embodiments of the present disclosure.

The difference between the jaw position detection apparatus in the present embodiment and that in Embodiment 1 is that the conversion mechanism 3 is implemented through another implementation manner. As shown in FIG. 6, the conversion mechanism 3 includes connecting rods 35 and sliders 36. An end of the connecting rod 35 is hinged to the connecting component 2, another end of the connecting rod 35 is hinged to the slider 36, and the slider 36 is connected to the displacement sensor 4. In this way, since a length of the connecting rod 35 is fixed, and a distance between the connecting component 2 and the slider 36 gradually changes when the connecting component 2 moves in the arc, the connecting rod 35 pushes the slider 36 to slide linearly. That is, a slider-crank mechanism constituted by the above solution may also convert the arcuate motion of the connecting rod 2 into the linear motion, thereby facilitating the displacement sensor 4 to detect the displacement information of the linear motion of the output end of the conversion mechanism 3, and then obtaining the position information of the jaw 1.

It will be noted that, referring to FIG. 6, the slider 36 also requires a corresponding sliding rail structure 37 to slide, and the slider 36 is pushed by the connecting rod 35 to slide linearly along the sliding rail structure 37. Of course, other components of the jaw position detection apparatus in some present embodiment, such as the connecting component 2 and the displacement sensor 4, are similar to those in Embodiment 1, and only need to be adaptively matched and mounted.

On the other hand, some embodiments of the present disclosure provide a medical accelerator treatment head. The medical accelerator treatment head includes at least one jaw 1 moving in an arc, and further includes the jaw position detection apparatus mentioned in the above embodiments.

Since the jaw 1 moves in an arc, after the medical accelerator treatment head provided by some embodiments of the present disclosure includes the above jaw position detection apparatus, the medical accelerator treatment head may effectively detect the position information of the jaw 1, is able to adapt to a large amount of irradiation, is not easily damaged, and has a high detection accuracy.

Figure 4:
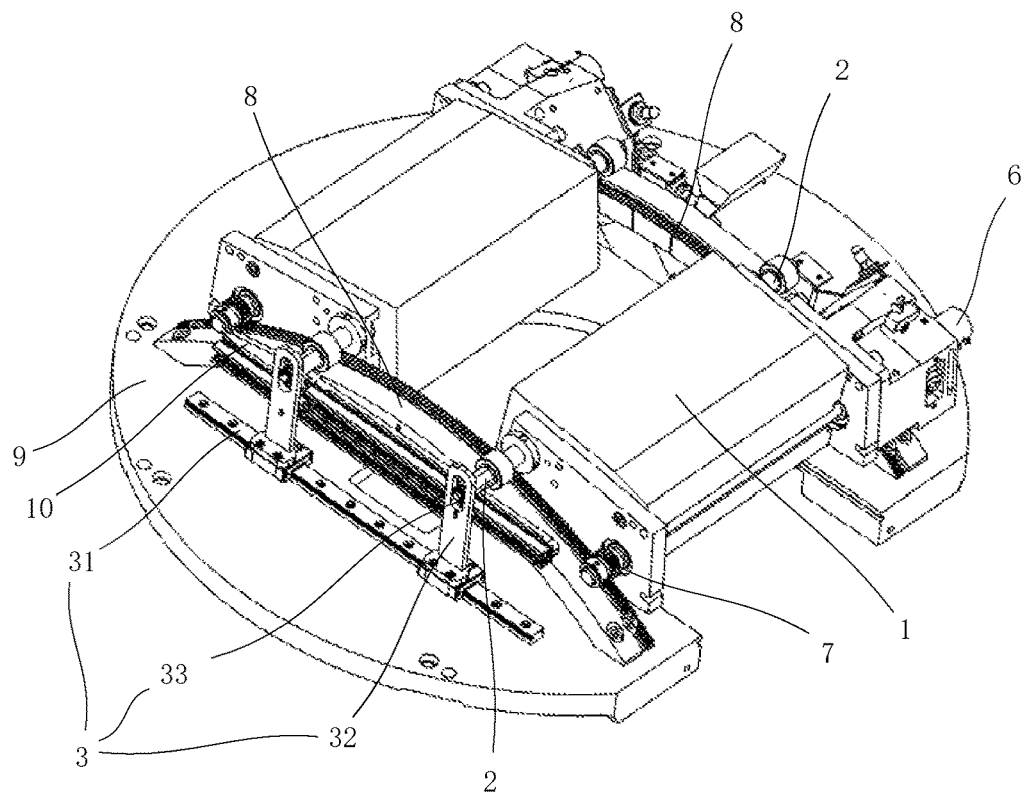
FIG. 4 is a first schematic diagram showing a three-dimensional structure of a jaw position detection apparatus in a case of two jaws, according to some embodiments of the present disclosure.
Figure 5:
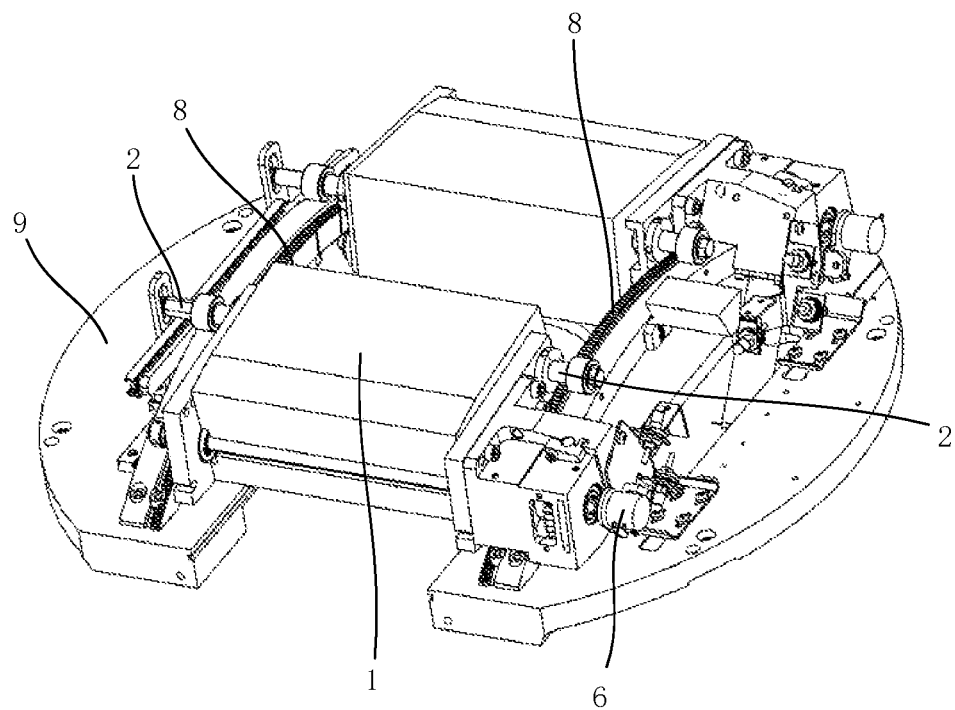
FIG. 5 is a second schematic diagram showing a three-dimensional structure of a jaw position detection apparatus in the case of two jaws, according to some embodiments of the present disclosure.

It will be noted that the jaw 1 moves in an arc for a better treatment, which has a plurality of implementation manners. The manner as shown in FIG. 1, FIG. 4 and FIG. 5, is an implementation manner. The medical accelerator treatment head in some embodiments of the present disclosure further includes motor(s) 6, rotary gear(s) 7 and arc gear ring(s) 8. The rotary gear 7 is connected to the jaw 1, and the rotary gear 7 moves in an arc along the arc gear ring 8 under driving of a motor 6.

In the medical accelerator treatment head of some embodiments of the present disclosure, the jaw 1 needs to move in an arc along the arc gear ring 8, the sliding component 32 of the jaw position detection apparatus needs to slide along the linear guide 31, and the extension shaft 42 of the displacement sensor 4 needs to slide along the variable resistance sliding rail 41. These similar guide rail mechanisms need to be fixed to ensure the motion of the corresponding moving components thereon. Therefore, referring to FIGS. 1, 4 and 5, the medical accelerator treatment head also includes an arc gear ring mounting base 9, such that the arc gear ring 8 may be mounted on the arc gear ring mounting base 9. Of course, similarly, the linear guide 31 of the jaw position detection apparatus may be fixed on the arc gear ring mounting base 9, and the variable resistance sliding rail 41 of the displacement sensor 4 may also be fixed on the arc gear ring mounting base 9. Referring to FIG. 1, in order to facilitate the layout, the variable resistance sliding rail 41 of the displacement sensor 4 may also be fixed on a side of the arc gear ring 8 proximate to the sliding component 32. Of course, the variable resistance sliding rail 41 of the displacement sensor 4 may be fixed on the sensor mounting base 10. A final purpose of the above arrangement of the linear guide 31 and the variable resistance sliding rail 41 is relatively fixed to the arc gear ring 8 to ensure normal motion of the moving components in the entire mechanism.

The orthographic projection of the arc gear ring 8 on the arc gear ring mounting base 9 extends in the first direction. The second direction is parallel to the beam direction, and is perpendicular to the arc gear ring mounting base 9.

In addition, in an actual structure, there are generally a plurality of jaws 1. In order to simplify the structure and facilitate the layout, the jaw position detection apparatus in some embodiments of the present disclosure may detect the position information of the plurality of jaws 1 at a time. For example, as shown in FIG. 1, there are two jaws 1, which are matched with two ends of the arc gear ring 8. In this way, the two jaws 1 share one arc gear ring 8 and one linear guide 31, and the number of other corresponding components (e.g., the sliding components 32 and the displacement sensors 4) is all two. A case that there are two jaws 1 is taken as an example, in order to facilitate the layout and make the motion of the jaw 1 more stable, as shown in FIGS. 4 and 5, the connecting component 2 may extend through the jaw 1 and both ends of which provide with bearings. Moreover, the number of corresponding arc gear rings 8 is also two, and both the two arc gear rings 8 are provided with tracks that are matched with the bearings 5 at both ends of the connecting component 2. Correspondingly, two rotary gears 7 may be disposed at two sides of the jaw 1 corresponding to the two arc gear rings 8, and the two rotary gears 7 are matched with the two arc gear rings 8. In this way, a process of the jaw 1 moving in the arc along the arc gear rings 8 is more stable.

The foregoing descriptions are merely some specific implementation manners of the present disclosure, but the protection scope of the present disclosure is not limited thereto, and changes or replacements that any person skilled in the art can easily think of in the technologies disclosed by the present disclosure should be within the protection scope of the present disclosure. Therefore, the protection scope of the present disclosure shall be subjected to the protection scope of the claims.

What is claimed is:

1. A jaw position detection apparatus, configured to detect position information of at least one jaw moving in an arc, the jaw position detection apparatus comprising:
   a connecting component fixed on a jaw;
   a conversion mechanism connected to the connecting component; wherein the conversion mechanism is configured to convert an arcuate motion of the connecting component into a linear motion when the connecting component moves in an arc with the jaw; and
   a displacement sensor connected to the conversion mechanism, and configured to detect displacement information of the linear motion of the conversion mechanism.

2. The jaw position detection apparatus according to claim 1, wherein the conversion mechanism includes a linear guide extending in a first direction and a sliding component slidable along the linear guide;
   the sliding component is provided with a first sliding groove and a second sliding groove along a second direction, an end portion of the connecting component is matched with and extended into the first sliding groove, the displacement sensor is connected to the second sliding groove; and
   the second direction is perpendicular to the first direction.

3. The jaw position detection apparatus according to claim 2, wherein a distance of the first sliding groove extending in the second direction is greater than or equal to a maximum displacement of the connecting component in the second direction when the connecting component moves in the arc.

4. The jaw position detection apparatus according to claim 2, wherein the end portion of the connecting component is sleeved with a bearing, and an outer wall of the bearing abuts against an inner wall of the first sliding groove, which extends in the second direction.

5. The jaw position detection apparatus according to claim 4, wherein the bearing is a rolling bearing.

6. The jaw position detection apparatus according to claim 2, wherein the displacement sensor includes a variable resistance sliding rail and an extension shaft; the variable resistance sliding rail extends in the first direction, a first end of the extension shaft is slidable along the variable resistance sliding rail, and a second end of the extension shaft is fixedly connected to the second sliding groove of the sliding component.

7. The jaw position detection apparatus according to claim 1, wherein the conversion mechanism includes a connecting rod and a slider; wherein an end of the connecting rod is hinged to the connecting component, and another end of the connecting rod is hinged to a slider, and the slider is connected to the displacement sensor.

8. The jaw position detection apparatus according to claim 1, wherein the displacement sensor is a linear displacement sensor.

9. A medical accelerator treatment head, comprising at least one jaw, the at least one jaw configured to move in an arc, the medical accelerator treatment head further comprising a jaw position detection apparatus, wherein the jaw position detection apparatus includes:
   a connecting component, fixed on a jaw;
   a conversion mechanism, connected to the connecting component wherein the conversion mechanism is configured to convert an arcuate motion of the connecting component into a linear motion when the connecting component moves in an arc with the jaw; and
   a displacement sensor, connected to the conversion mechanism, and configured to detect displacement information of the linear motion of the conversion mechanism.

10. The medical accelerator treatment head according to claim 9, the medical accelerator treatment head further comprising:
    at least one motor;
    an arc gear ring; and
    at least one rotary gear; wherein each rotary gear is connected to one jaw, and the rotary gear is configured to move in an arc along the arc gear ring under driving of a motor.

11. The medical accelerator treatment head according to claim 10, further comprising an arc gear ring mounting base, wherein the arc gear ring is mounted on the arc gear ring mounting base.

12. The medical accelerator treatment head according to claim 11, wherein the conversion mechanism includes a linear guide extending in a first direction and a sliding component slidable along the linear guide;
    the sliding component is provided with a first sliding groove and a second sliding groove along a second direction, an end portion of the connecting component is matched with and extended into the first sliding groove, the displacement sensor is connected to the second sliding groove; and the second direction is perpendicular to the first direction.

13. The medical accelerator treatment head according to claim 12, wherein the linear guide of the jaw position detection apparatus is fixed on the arc gear ring mounting base.

14. The medical accelerator treatment head according to claim 13, wherein the displacement sensor includes a variable resistance sliding rail and an extension shaft; the variable resistance sliding rail extends in the first direction, a first end of the extension shaft is slidable along the variable resistance sliding rail, and a second end of the extension shaft is fixedly connected to the second sliding groove of the sliding component; and the variable resistance sliding rail is fixed on the arc gear ring.

15. The medical accelerator treatment head according to claim 13, wherein the displacement sensor includes a variable resistance sliding rail and an extension shaft; the variable resistance sliding rail extends in the first direction, a first end of the extension shaft is slidable along the variable resistance sliding rail, and a second end of the extension shaft is fixedly connected to the second sliding groove of the sliding component; and the variable resistance sliding rail is fixed on the arc gear ring mounting base.

16. A medical accelerator treatment head, comprising:

at least one jaw, configured to move in an arc;

a jaw position detection apparatus; wherein the jaw position detection apparatus includes:

a connecting component fixed on a jaw;

a conversion mechanism connected to the connecting component; wherein the conversion mechanism is configured to convert an arcuate motion of the connecting component into a linear motion when the connecting component moves in an arc with the jaw;

a displacement sensor, connected to the conversion mechanism, and configured to detect displacement information of the linear motion of the conversion mechanism;

at least one motor;

two arc gear rings; and a plurality of rotary gears, wherein two rotary gears are disposed at two sides of each jaw corresponding to the two arc gear rings, and the two rotary gears are matched with the two arc gear rings; and wherein the two rotary gear are configured to move in an arc along the two arc gear rings under driving of a motor.

17. The medical accelerator treatment head according to claim 16, further comprising an arc gear ring mounting base, wherein the two arc gear rings are mounted on the arc gear ring mounting base.

18. The medical accelerator treatment head according to claim 17, wherein the conversion mechanism includes a linear guide extending in a first direction and a sliding component slidable along the linear guide;

the sliding component is provided with a first sliding groove and a second sliding groove along a second direction, an end portion of the connecting component is matched with and extended into the first sliding groove, the displacement sensor is connected to the second sliding groove;

the second direction is perpendicular to the first direction; and the linear guide of the jaw position detection apparatus is fixed on the arc gear ring mounting base.

19. The medical accelerator treatment head according to claim 18, the displacement sensor includes a variable resistance sliding rail and an extension shaft; the variable resistance sliding rail extends in the first direction, a first end of the extension shaft is slidable along the variable resistance sliding rail, and a second end of the extension shaft is fixedly connected to the second sliding groove of the sliding component; and the variable resistance sliding rail is fixed on an arc gear ring.

20. The medical accelerator treatment head according to claim 18, wherein the displacement sensor includes a variable resistance sliding rail and an extension shaft; the variable resistance sliding rail extends in the first direction, a first end of the extension shaft is slidable along the variable resistance sliding rail, and a second end of the extension shaft is fixedly connected to the second sliding groove of the sliding component; and the variable resistance sliding rail is fixed on the arc gear ring mounting base.

* * * * *